United States Patent
Franke et al.

(10) Patent No.: US 10,434,303 B2
(45) Date of Patent: Oct. 8, 2019

(54) METHOD AND APPARATUS FOR DIRECTED PROPAGATION OF NEURAL STIMULATION

(71) Applicant: Cardiac Pacemakers, Inc., St. Paul, MN (US)

(72) Inventors: Manfred Franke, Weissenborn Sa. (DE); David J. Ternes, Roseville, MN (US); Juan Gabriel Hincapie Ordonez, Maple Grove, MN (US); Stephen B. Ruble, Lino Lakes, MN (US); Jason J. Hamann, Blaine, MN (US); Kevin J. Mohsenian, Mequon, WI (US); Jack Gordon, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 273 days.

(21) Appl. No.: 14/596,409

(22) Filed: Jan. 14, 2015

(65) Prior Publication Data

US 2015/0202433 A1    Jul. 23, 2015

Related U.S. Application Data

(60) Provisional application No. 61/928,781, filed on Jan. 17, 2014.

(51) Int. Cl.
*A61N 1/05* (2006.01)
*A61N 1/36* (2006.01)

(52) U.S. Cl.
CPC ......... *A61N 1/0556* (2013.01); *A61N 1/0551* (2013.01); *A61N 1/36053* (2013.01); *A61N 1/36114* (2013.01)

(58) Field of Classification Search
CPC .................................................. A61N 1/0556
See application file for complete search history.

(56) References Cited

U.S. PATENT DOCUMENTS

| 4,602,624 A | 7/1986 | Naples et al. |
| 4,608,985 A | 9/1986 | Crish et al. |

(Continued)

FOREIGN PATENT DOCUMENTS

| DE | 202010015346 U1 * | 3/2011 | ........... A61N 1/0556 |
| WO | WO-9215366 A1 | 9/1992 | |
| WO | WO-9320887 A1 | 10/1993 | |
| WO | WO-2015108909 A1 | 7/2015 | |

OTHER PUBLICATIONS

Franke, Manfred, et al., "Depletion Block to Block Nerve Communication", U.S. Appl. No. 61/928,725, filed Jan. 17, 2014.

(Continued)

*Primary Examiner* — Carl H Layno
*Assistant Examiner* — Jennifer L Ghand
(74) *Attorney, Agent, or Firm* — Schwegman Lundberg & Woessner, P.A.

(57) ABSTRACT

A neural stimulation system delivers neural stimulation to a target nerve with control of direction of propagation of evoked neural signals in one or more fiber types of the target nerve using electrode configuration, thereby providing effective therapy while minimizing unintended effects. In various embodiments, mechanical parameters of a multipolar electrode are determined to provide directed propagation of the neural stimulation by effecting neural conduction block in or near the stimulation site. In various embodiments, the electrode includes a cathode for evoking action potentials and a plurality of anodes for blocking the propagation of the evoked action potentials in specified direction(s) and fiber type(s) while minimizing the formation of virtual cathodes.

20 Claims, 13 Drawing Sheets

(56) References Cited

U.S. PATENT DOCUMENTS

| | | | |
|---|---|---|---|
| 4,628,942 A | 12/1986 | Sweeney et al. | |
| 4,649,936 A | 3/1987 | Ungar et al. | |
| 5,324,322 A * | 6/1994 | Grill, Jr. | A61N 1/0556 600/375 |
| 2003/0045909 A1 | 3/2003 | Gross et al. | |
| 2003/0236557 A1 | 12/2003 | Whitehurst et al. | |
| 2006/0116739 A1 * | 6/2006 | Betser | A61N 1/0556 607/48 |
| 2007/0112402 A1 * | 5/2007 | Grill | A61N 1/375 607/115 |
| 2008/0132983 A1 * | 6/2008 | Cohen | A61N 1/0551 607/118 |
| 2011/0160822 A1 * | 6/2011 | Jackson | A61N 1/056 607/116 |
| 2014/0364921 A1 | 12/2014 | Legay et al. | |
| 2014/0364923 A1 | 12/2014 | Legay et al. | |

OTHER PUBLICATIONS

Franke, Manfred, et al., "Selective Nerve Stimulation Using Presynaptic Terminal Depletion Block", U.S. Appl. No. 61/928,732, filed Jan. 17, 2014.

Franke, Manfred, et al., "Systems and Methods for Delivering Pulmonary Therapy", U.S. Appl. No. 61/928,714, filed Jan. 17, 2014.

Franke, Manfred, et al., "Systems and Methods for Selective Stimulation of Nerve Fibers in Carotid Sinus", U.S. Appl. No. 61/928,707, filed Jan. 17, 2014.

"International Application Serial No. PCT/US2015/011305, International Preliminary Report on Patentability dated Jul. 28, 2016", 9 pgs.

"International Application Serial No. PCT/US2015/011305, International Search Report dated Apr. 17, 2015", 4 pgs.

"International Application Serial No. PCT/US2015/011305, Written Opinion dated Apr. 17, 2015", 7 pgs.

* cited by examiner

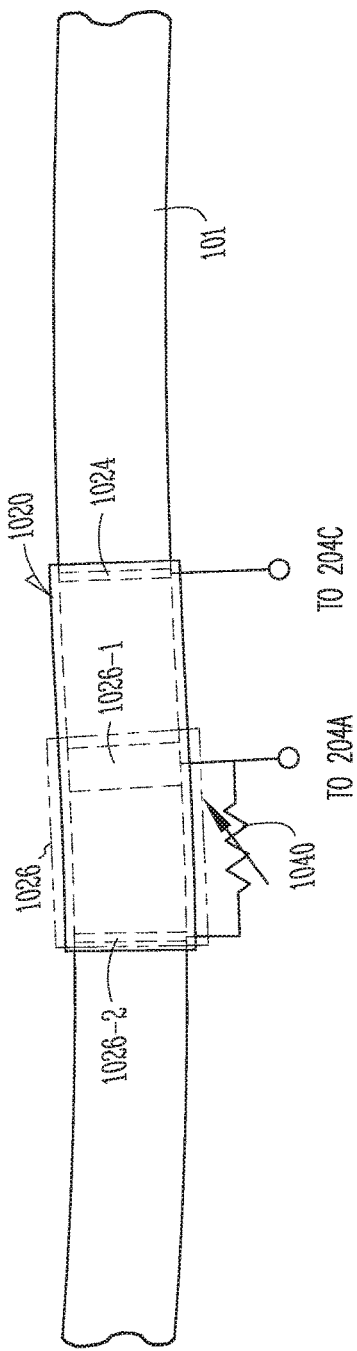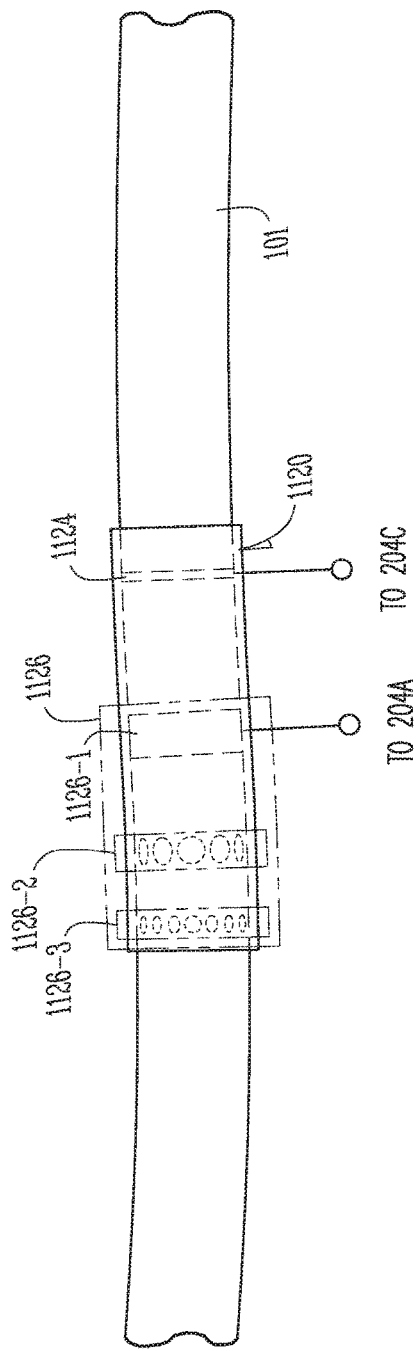

METHOD AND APPARATUS FOR DIRECTED PROPAGATION OF NEURAL STIMULATION

CLAIM OF PRIORITY

This application claims the benefit of priority under 35 U.S.C. § 119(e) of U.S. Provisional Patent Application Ser. No. 61/928,781, filed on Jan. 17, 2014, which is herein incorporated by reference in its entirety.

TECHNICAL FIELD

This document relates generally to neural stimulation and more particularly to method and apparatus for controlling direction of propagation of neural signals evoked by electrical stimulation.

BACKGROUND

Neural stimulation has been proposed as a therapy for a number of conditions. Neural stimulation may be delivered to modulate the autonomic system, which may be referred to as an autonomic modulation therapy (AMT). Examples of AMT include therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

A target nerve for delivering neural stimulation, such as the vagus nerve in AMT, may be connected to multiple organs to control their various functions. The neural stimulation when delivered to a stimulation site may evoke neural signals (action potentials) that propagate in both directions to multiple organs to result in intended and unintended modulation of their functions. Thus, there is a need for controlling the neural stimulation to ensure efficacy of the intended therapy while minimizing unintended effects.

SUMMARY

A neural stimulation system delivers neural stimulation to a target nerve with control of direction of propagation of evoked neural signals in one or more fiber types of the target nerve using electrode configuration, thereby providing effective therapy while minimizing unintended effects. In various embodiments, mechanical parameters of a multipolar electrode are determined to provide directed propagation of the neural stimulation by effecting neural conduction block in or near the stimulation site. In various embodiments, the electrode includes a cathode for evoking action potentials and a plurality of anodes for blocking the propagation of the evoked action potentials in specified direction(s) and fiber type(s) while minimizing the formation of virtual cathodes.

In one embodiment, a system for delivering stimulation includes an electrode configured to deliver electrical stimulation pulses to a nerve at a stimulation site. The electrode includes a substrate with a cathode and a plurality of anodes formed on the cuff substrate. The cathode is configured to allow the electrical stimulation pulses to evoke action potentials. The plurality of anodes are shaped, sized, and arranged to effect neural conduction block without forming a virtual cathode. The neural conduction block includes blocking of propagation of the evoked action potentials front the cathode in one or more fiber types of the nerve.

In one embodiment, a method for delivering stimulation is provided. The method includes providing a substrate and forming a cathode and a plurality of anodes on the substrate such that an electrode for delivering electrical stimulation pulses to a nerve at a stimulation site is formed. The shape, size, and arrangement of the cathode and the plurality of anode are determined such that action potentials are evoked in a portion of the nerve adjacent the cathode and neural conduction block is effected without forming a virtual cathode. The neural conduction block includes blocking of propagation of the evoked action potentials from the cathode in one or more fiber types.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 10 is an illustration of an embodiment of a nerve cuff electrode with impedance coupled anodes.

FIG. 11 is an illustration of an embodiment of a nerve cuff electro with anodes each including an array of conductive contacts.

DETAILED DESCRIPTION

Figure 1:
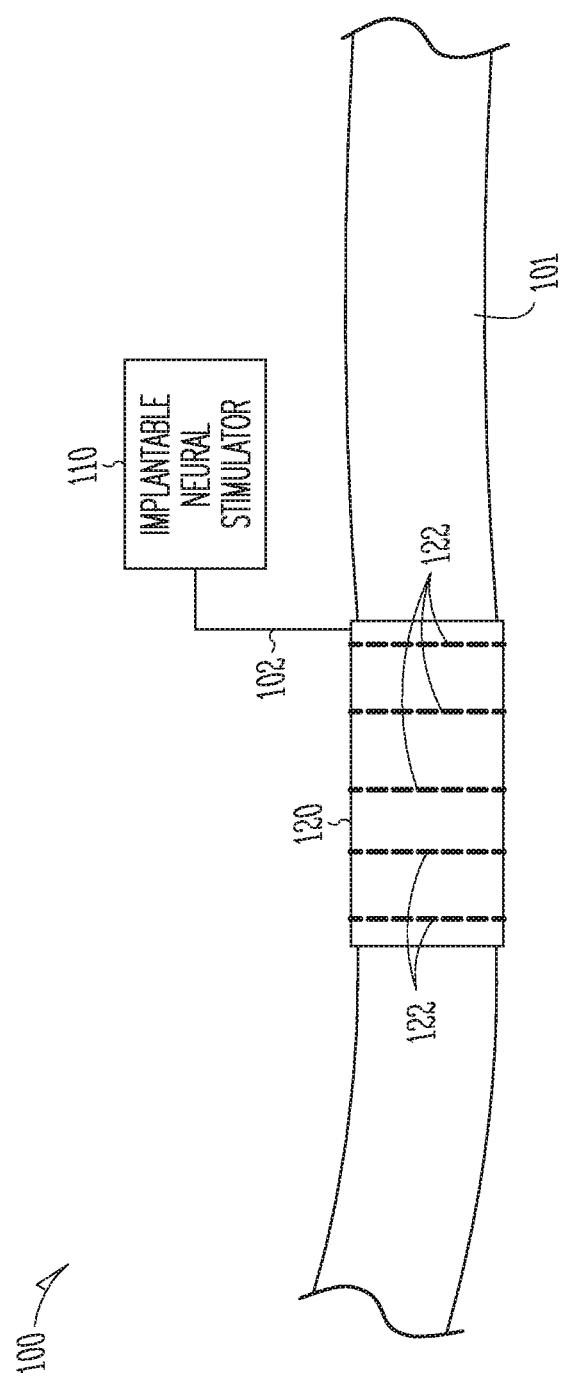
FIG. 1 is an illustration of an embodiment of a neural stimulation system and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", one", or "various" embodiments in this disclosure are not necessarily to the same embodiment, and such references contemplate more than one embodiment.

This document discusses a method and system for controlling direction of propagation of neural signals evoked by neural stimulation in one or more types of nerve fibers in a target nerve to which the neural stimulation is delivered. In various embodiments, the neural stimulation is delivered in a form of electrical stimulation pulses through a multi-polar electrode that includes at least one cathode and a plurality of anodes. The cathode and anodes are configured with mechanical parameters selected to allow for the directed propagation of the evoked neural signals by effecting controlled neural conduction block in the one or more types of nerve fibers in the target nerve. In various embodiments, the mechanical parameters geometrically describe size, shape, and location of the cathode and each of the anodes in the multi-polar electrode. In various embodiments, the mechanical parameters are selected such that the desirable neural conduction block occurs substantially within the portion of the target nerve wrapped in the multi-polar electrode at the stimulation site. In some embodiments, the desirable neural conduction block includes blocking in one or more specified fiber types. In various embodiments, this allows for control of direction of propagation of the evoked neural signals with differentiation between myelinated fibers of different sizes and between myelinated and umnyelinated fibers. In various other embodiments, this allows for control of direction of propagation of the evoked neural signals with differentiation between efferent and afferent fibers.

In this document, "a plurality of anodes" of a multi-polar electrode refers to the multiple conductive contacts within the multi-polar electrode such as a nerve cuff electrode) that are configured to act as anodes. In some embodiments, all the anodes contacts) of the plurality of anodes are electrically connected to each other and can be connected to a stimulation output channel using a single conductor. This may be considered as a single anode having multiple contacts. In some other embodiments, the anodes may be connected to two or more stimulation output channels using two or more conductors.

In this document, multi-polar nerve cuff electrodes are specifically discussed as examples of the multi-polar electrode, while the present subject matter is not limited to nerve cuff electrodes. Other forms of the multi-polar electrode include may be used without departing from the spirit and scope of the present invention.

FIG. 1 is an illustration of an embodiment of a neural stimulation system 100 and portions of an environment in which system 100 is used. System 100 includes an implantable neural stimulator 110, a nerve cuff electrode 120 shown as being wrapped around a nerve 101 at a stimulation site, and a lead 102 connecting nerve cuff electrode 120 to implantable neural stimulator 110. Implantable neural stimulator 110 delivers neural stimulation such as in the form of electrical stimulation pulses through nerve cuff electrode 120 to evoke neural signals (action potentials). Nerve cuff electrode 120 (also referred to as an electrode assembly) includes a plurality of electrodes (conductive contacts) 122 that are shaped, sized, and arranged to effect neural conduction block substantially within the portion of nerve 101 wrapped within nerve cuff electrode 120. The neural conduction block includes blocking of propagation of the evoked neural signals between electrodes 122 in one or more fiber types of nerve 101, thereby resulting in directed propagation of the evoked neural signals in the one or more fiber types.

Nerve 101 represents any nerve being selected as a target for delivering the neural stimulation using system 100 in various embodiments. In one example, nerve 101 is the vagus nerve as the target nerve for AMT. Examples of stimulation site (portion of nerve 101 onto which nerve cuff electrode 120 is applied) on the vagus nerve of a patient include, but are not limited to, the cervical spinal level between the thyroid cartilage and the sternum of the patient and cardiac branches of the vagus nerve caudal to the branching of the recurrent laryngeal nerve. Other examples of nerve 101 include hypoglossal nerve, glossopharyngeal nerve, carotid sinus nerve, symptathetic nerves, phrenic nerves, renal nerves, and splanchnic nerves. Examples of the stimulation sites include cranial or spinal nerves outside or near the spinal cord and dorsal root ganglia.

Figure 2:
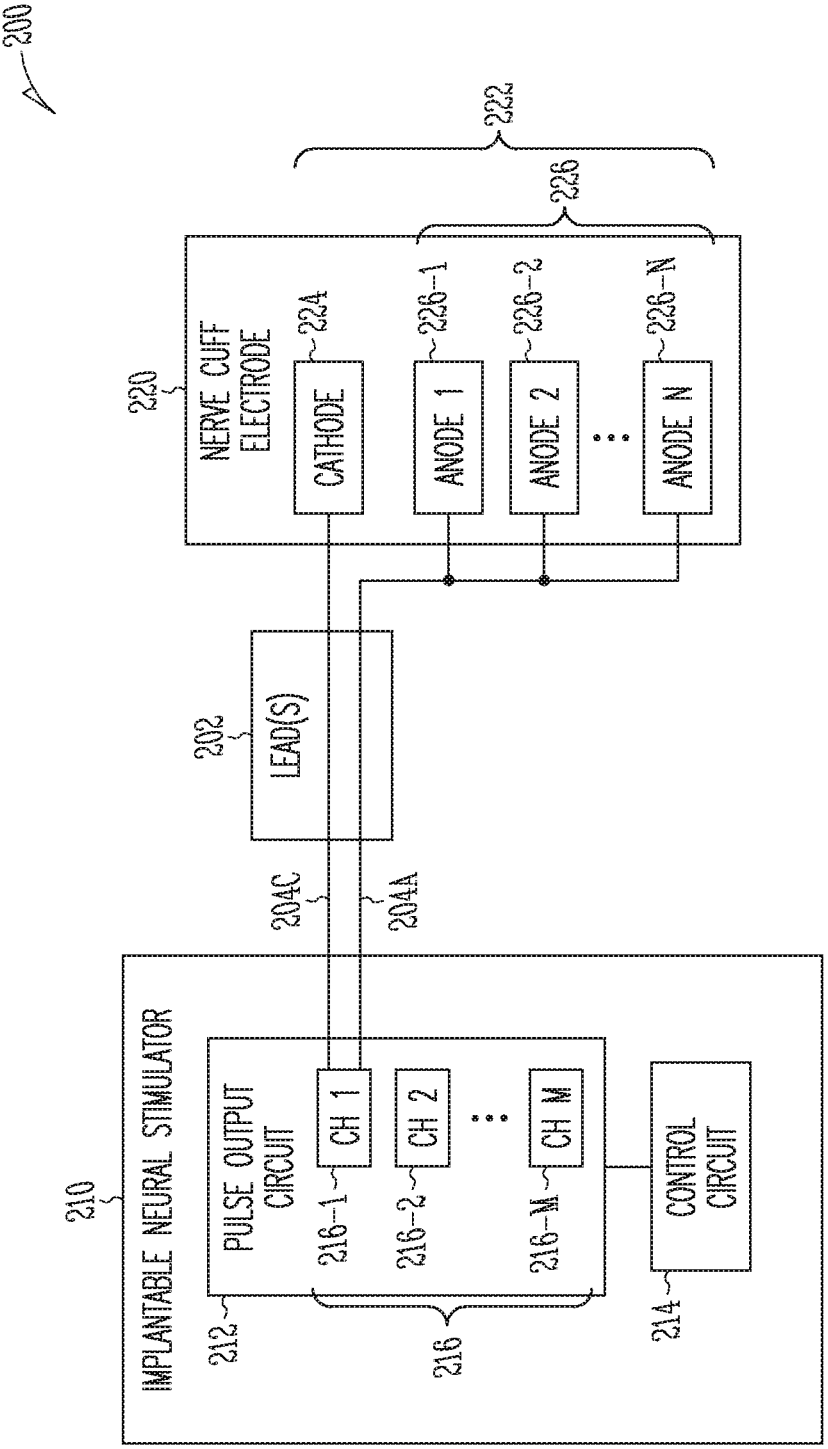
FIG. 2 is a block, diagram illustrating an embodiment of the neural stimulation system.

FIG. 2 is a block diagram illustrating an embodiment of a neural stimulation system 200, which represents an example of system 100. System 200 as shown in FIG. 2 includes an implantable neural stimulator 210, a nerve cuff electrode 220, and one or more leads 202 connecting nerve cuff electrode 220 to implantable neural stimulator 210. In various embodiments, system 200 can include one or more nerve cuff electrodes each connected to implantable neural stimulator 210 via one or more leads.

Implantable neural stimulator 210 represents an example of implantable neural stimulation 110 and includes a pulse output circuit 212 configured to deliver electrical stimulation pulses and a control circuit 214 configured to control the delivery of the electrical stimulation pulses using a plurality of stimulation parameters. Pulse output circuit 212 includes one or more independently controllable output channels 216-1, 216-2, . . . 216-M (M≥1), which are also referred to as current sources when they deliver the electrical stimulation pulses with constant-current waveforms. In various embodiments, control circuit 214 controls the delivery of the electrical stimulation pulses from each channel of channels 216-1 through 216-M using channel parameters of the plurality of stimulation parameters that are programmed for that channel. In various embodiments, programmable parameters of the channel parameters include, for example, pulse (current) amplitude, pulse width, pulse frequency (or inter-pulse interval), duty cycle, and stimulation duration (therapy session duration).

Nerve cuff electrode 220 represent an example of nerve cuff electrode 120, and is configured for delivering the electrical stimulation pulses to nerve 100 at the stimulation site. In various embodiments, nerve cuff electrode 220 includes a plurality of electrodes (conductive contacts) 222. In the illustrated embodiment, electrodes 222 include a cathode 224 and a plurality of anodes 226. In various embodiments, anodes 226 includes anodes 226-1, 216-2, . . . 226-N (N≥2). Cathode 224 and anodes 226 are configured to allow the electrical stimulation pulses to be delivered to nerve 101 when nerve cuff electrode 220 is wrapped around the portion of nerve 101 at the stimulation site. In various embodiments, cathode 224 and anodes 226 are configured to effect directed propagation of neural signals (action potentials) evoked by the electrical stimulation pulses along nerve 101. The electrical stimulation pulses each depolarize the membrane of nerve 101 at the site of cathode 224 to evoke an action potential, and hyperpolarize the membrane of nerve 101 at the site of a blocking anode of anodes 226 to block propagation of the evoked action potential traveling from cathode 224 to the blocking anode. In various embodiments, anodes 226 are shaped, sized, and arranged to effect neural conduction block substantially within the portion of the nerve wrapped within nerve cuff electrode 220. The neural conduction block includes blocking of propagation of the evoked neural signals in one or more directions for at least a portion of nerve 101. In various embodiments, the neural conduction block is controllably effected in one or more fiber types in nerve 101. In other words, the neural conduction block may be selectively applied to one or more specified type of nerve fibers. For example, depending on the purpose of the neural stimulation, the neural conduction block may be intended to apply on nerve fibers of certain diameters. In some embodiments, this allows for blocking of myelinated fibers of selected diameter range, either myelinated fibers or unmyelinated fibers, or either the efferent fibers or the afferent fibers. In some embodiments, anodes 226 are shaped, sized, and arranged to allow the electrical stimulation pulses to provide a graded electric field in and around the portion of nerve 101 wrapped within nerve cuff electrode 220.

Lead(s) 202 represent(s) an example of lead 102. In the illustrated embodiment, lead(s) 202 include(s) a cathode conductor 204C and an anode conductor 204A. Cathode conductor 204C provides an electrical connection between cathode 224 and output channel 216-1. Anode conductor 204A provides an electrical connection connecting all of anodes 226 to output channel 216-1. In various embodiments, lead(s) 202 may include a single lead including both cathode conductor 204C and anode conductor 204A, or one lead including cathode conductor 204C and another lead including anode conductor 204A. In various embodiments, lead(s) 202 may include cathode conductor 204C and one or more anode conductors 204A each configured to provide an electrical connection between an anode of anodes 226 and output channel 216-1. In various embodiments where system 200 includes multiple nerve cuff electrodes, one or more leads similar to lead(s) 202 can be used to provide electrical connections each between one of the nerve cuff electrodes and one of the output channels 216-1 through 216-M.

Figure 3:
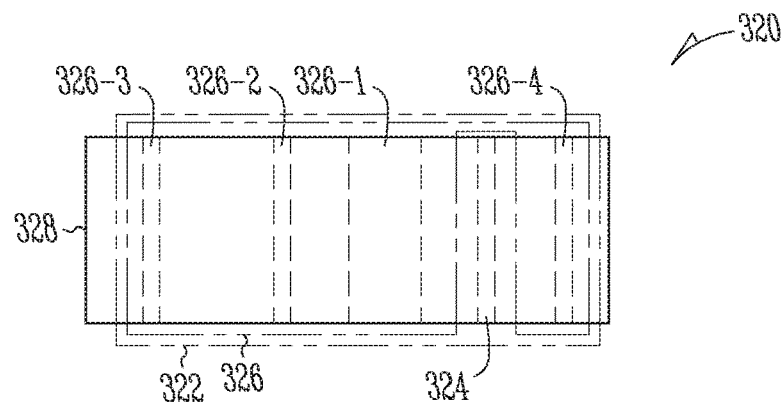
FIG. 3 is an illustration of an embodiment of a nerve cuff electrode of the neural stimulation system shown in a curled (relaxed) state.
Figure 4:
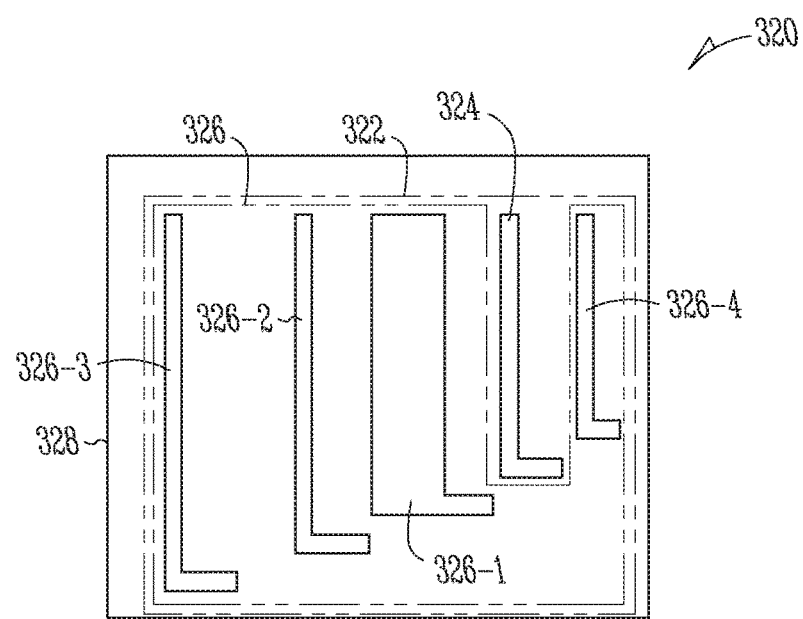
FIG. 4 is an illustration of an embodiment of the nerve cuff electrode shown in an open (uncurled) state.

FIG. 3 is an illustration of an embodiment of a nerve cuff electrode 320, which represents an example of nerve cuff electrode 220 and is shown in a curled (relaxed) state. FIG. 4 is an illustration of an embodiment of nerve cuff electrode 320 shown in an open (uncurled) state. Nerve cuff electrode 320 includes a cuff substrate 328 and a plurality of electrodes (conductive contacts) 322 formed on cuff substrate 328. In various embodiments, cuff substrate 328 includes a self-curling sheet configured to be wrapped around a portion of nerve 101 at the stimulation site. In one embodiment, cuff substrate 326 includes a self-curling silicone sheet. Electrodes 322 represent an example of electrodes 222 and includes a cathode 324 representing an example of cathode 224 and anodes 326-1, 326-2, 326-3, and 326-4 representing an example of anodes 226-1 through 226-N (where N=4). Cathode 324 is configured to allow the electrical stimulation pulses to evoke action potentials in nerve 101. Anodes 326-1, 326-2, 326-3, and 326-4 are shaped, sized, and arranged to effect neural conduction block substantially within the portion of nerve 101 wrapped within nerve cuff electrode 320. The neural conduction block includes blocking of propagation of the evoked action potentials from cathode 324 in one or more fiber types.

Figure 5:
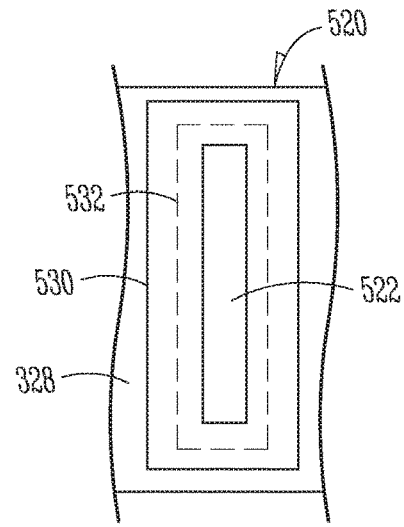
FIG. 5 is an illustration of an embodiment of an electrode (conductive contact) of the nerve cuff electrode.

FIG. 5 is an illustration of an embodiment of an electrode (conductive contact) 522 of a nerve cuff electrode 520 partially shown in an open (uncurled) state. Electrode 522 represents an example of structure of any cathode or anode of a nerve cuff electrode as discussed in this document, including cathode 224 and 324 and anodes 226-1 through 226-N and 326-1, 326-2, 326-3, and 326-4. Electrode 522 is a ring electrode formed on cuff substrate 328. The ring electrode is an approximately circular band suitable for encircling the portion of nerve 101 wrapped by nerve cuff electrode 520, which represents an example of nerve cuff electrode 320. The band is electrically conductive and faces nerve 101 when the portion of nerve 101 is wrapped by nerve cuff electrode 520. Mechanical (geometrical) parameters defining electrode 522 include, for example, the width of the band. In the illustrated embodiment, a conductive layer 532 such as a metal foil is affixed onto cuff substrate 328, and an insulation layer 530 is affixed onto at least conductive layer 532. Insulation layer 530 includes an opening exposing a portion of conductive layer 532 to form electrode (conductive contact) 522.

Figure 6:
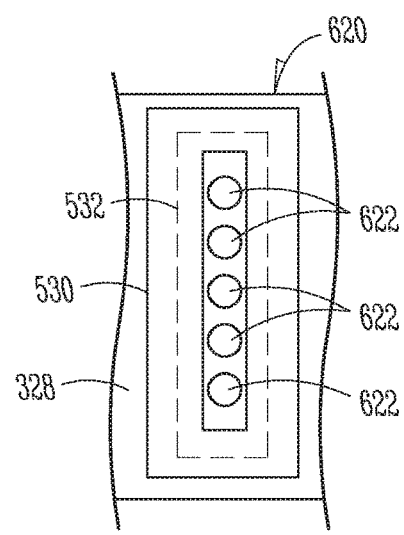
FIG. 6 is an illustration of another embodiment of an electrode (conductive contact) of the nerve cuff electrode.

FIG. 6 is an illustration of an embodiment of an electrode (conductive contact) 622 of a nerve cuff electrode 620 partially shown in an open (uncurled) state. Electrode 622 represents another example of structure of any cathode or anode of a nerve cuff electrode as discussed in this document, including cathode 224 and 324 and anodes 226-1 through 226-N and 326-1, 326-2, 326-3, and 326-4. Electrode 622 is a ring electrode formed on cuff substrate 328. The ring electrode includes an array of conductive contacts. The array is arranged to encircle the portion of nerve 101 wrapped by nerve cuff electrode 620, which represents another example of nerve cuff electrode 320. The conductive contacts face nerve 101 when the portion of nerve 101 is wrapped by nerve cuff electrode 620. Mechanical (geometrical) parameters defining electrode 622 include, for example, number of the conductive contacts, distance between adjacent conductive contacts of the array of conductive contacts, and size of each of the conductive contacts. The size can be measured by the area of each contact of the conductive contacts, or measured by the diameter when the conductive contacts are each approximately circular as in the illustrated embodiment. In the illustrated embodiment, conductive layer 532 is affixed onto cuff substrate 328, and insulation layer 530 is affixed onto at least conductive layer 532. Insulation layer 530 includes multiple openings exposing portions of conductive layer 532 to form electrode (conductive contact) 622.

In various embodiments, the plurality of electrodes in a nerve cuff electrode such as those discussed in this document, including nerve cuff electrode 120, 220, and 320, can include one or more electrodes constructed as electrode 522, one or more electrodes constructed as electrode 622, and/or one or more electrodes constructed in one or more other manners considered to be suitable by those skilled in the art.

In some embodiments, insulation layer 530 includes multiple openings grouped into multiple anodes each in the form of either electrode 522 or electrode 622.

Electrode Example for Directed Promotion

Figure 7:
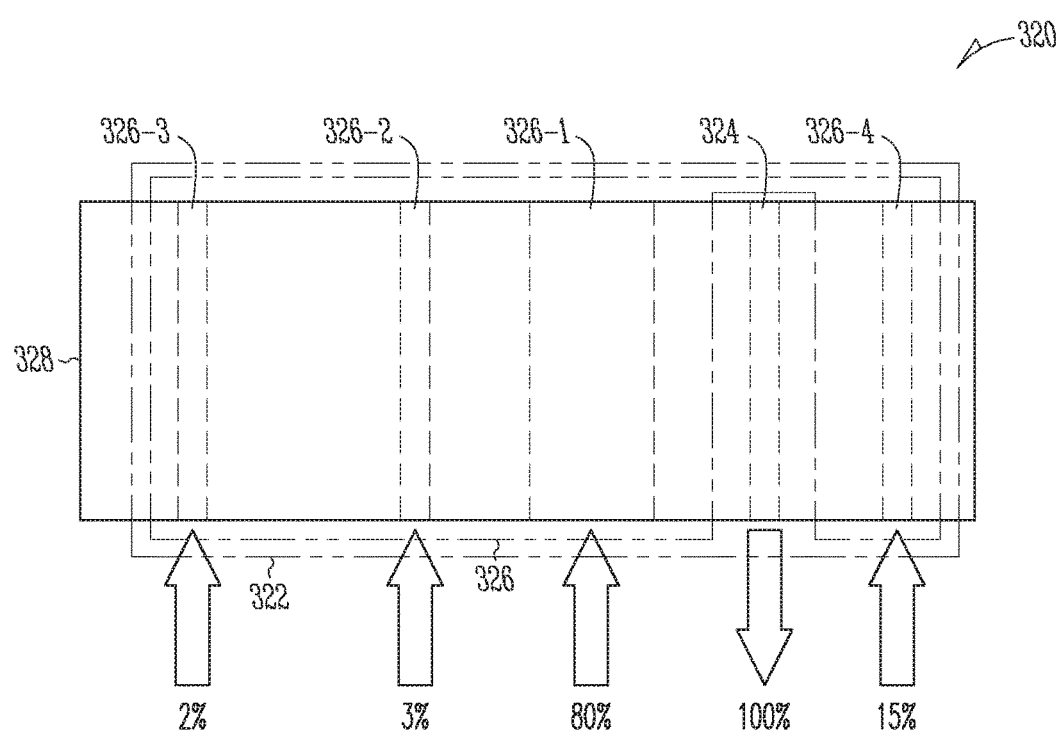
FIG. 7 is an illustration of an embodiment of a nerve cuff electrode configured to allow for directed propagation of evoked neural signals.

FIG. 7 is an illustration of an embodiment of nerve cuff electrode 320 with electrodes 322 configured to allow for directed propagation of the evoked neural signals along nerve 101. In various embodiments, the present subject matter provides a nerve cuff electrode that includes a cathode, a blocking anode, and one or more flanking anodes. In various embodiments, the nerve cuff electrode 320 has a length between approximately 3 and 30 mm and a diameter between approximately 1 and 5 ram (in its curled state). In the illustrated embodiment, anodes 326 of nerve cuff electrode 320 includes a blocking anode 326-1 and flanking anodes 326-2, 326-3, and 326-4. The electrical stimulation pulses delivered through nerve cuff electrode 320 each depolarize the membrane of nerve 101 at cathode 324 to evoke an action potential, and hyperpolarize the membrane of nerve 101 at blocking anode 326-1 to block propagation of the evoked action potential from cathode 324 to blocking anode 326-1. Flanking anodes 326-2, 326-3, and 326-4 are used to minimize formation of virtual cathodes (edge effect, creating new action potentials that propagate along nerve 101), thereby minimizing "leaking" of evoked neural signals that are to be blocked. In various embodiments, such neural conduction block is controlled by at least various mechanical (geometrical) parameters. Examples of the mechanical parameters controlling the distribution of the current flowing from cathode 324 to anodes 326 include width of blocking anode 326-1, number of the flanking anodes (3 in the illustrated embodiment), the width of each of flanking anodes 326-2, 326-3, and 326-4, and the location of each of anodes 326 with respect to cathode 324. In some embodiments, neural conduction block is controlled by the various mechanical (geometrical) parameters as well as electrical parameters such as amplitude (current) of the electrical stimulation pulse. In various embodiments, mechanical and/or electrical parameters are selected such that blocking anode 326-1 is used to effect the neural conduction block in one or more fiber types substantially throughout an entire cross-section of nerve 101, and flanking electrodes 326-2, 326-3, and 326-4 are used to minimize formation of the virtual cathodes. In the illustrated embodiment, anodes 326 are sized and arranged to result in a distribution of the current flowing from cathode 324, including approximately 80% to anode 326-1, 3% to anode 326-2, 2% to anode 326-3, and 15% to anode 326-4. The current flowing from anodes 326 to cathode 324 is the negative sum of the currents flowing through anodes 326. This distribution was found to effect neural conduction block substantially within the portion of nerve 101 wrapped within nerve cuff electrode 320 at the stimulation site.

Nerve cuff electrode 320 as illustrated in FIG. 7 is discussed herein as an example but not a limitation. Various embodiments use at least mechanical (geometrical) parameters to define electrodes in a nerve cuff electrode to allow for directed propagation of the evoked neural signals along a target nerve. The nerve cuff electrode in various embodiments includes a cathode, a blocking anode, and one or more flanking anodes. The electrical stimulation pulses delivered to the target nerve through the nerve cuff electrode each depolarize the membrane of the target at the cathode to evoke an action potential, and hyperpolarize the membrane of the target nerve at the blocking anode to block propagation of the evoked action potential in the direction from the cathode to the blocking anode. The blocking and flanking anodes are also sized and arranged to control formation of virtual cathodes (edge effect) within or adjacent to the nerve cuff electrode. In various embodiments, the blocking and flanking anodes are sized and arranged to effect uni-directional block in which at least a portion of the target nerve is blocked in one direction. This portion of the target nerve may include, for example, one or more fiber types. Example of the fiber types include myelinated and unmyelinated fibers, efferent and afferent fibers, and peripheral fibers (near the surface of the nerve, specified by depth or thickness from the surface of the nerve) and center fibers. Mechanical parameters of the nerve cuff electrode and/or parameters controlling the electrical stimulation pulses can be adjusted to control directed propagation of the evoked action potentials in selected fiber type(s) of the target nerve. In various embodiments, the blocking and flanking anodes are sized and arranged to effect multi-directional block in which at least a portion of the target nerve is blocked in the cranial, caudal, or both cranial and caudal directions. For example, the direction of propagation of the evoked action potentials can be controlled differently for each selected fiber type of the target nerve, thereby selectively modulating functions of different organs innervated by different fiber types of the target nerve.

Figure 8:
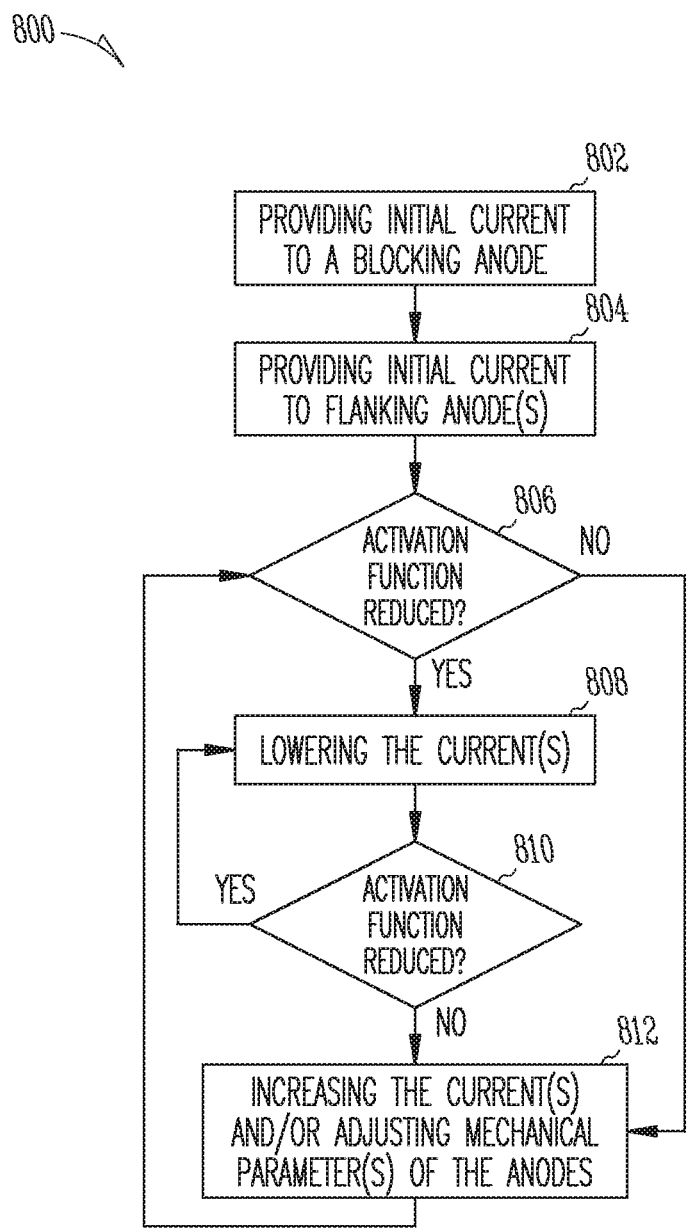
FIG. 8 is a flow chart illustrating a method for determining various parameters of the nerve cuff electrode of FIG. 7.

FIG. 8 is a flow chart illustrating a method 800 for determining various parameters of nerve cuff electrode 320 as illustrated in FIG. 7. In the illustrated embodiments, method 800 includes determination of both electrical and mechanical parameters. In some embodiments, methods 800 is applied to determine the mechanical parameters for nerve cuff electrode 320, with one or more electrical parameters controlling the electrical stimulation pulses set at specified values or value ranges that will be applied during therapies. In various embodiments, performance of method 800 can be computerized. For example, a program can be installed in a computer to allow for computerized optimization of the mechanical parameters and/or the one or more electrical parameters by performing all of selected steps of method 800.

At 802, an initial amount of blocking current is applied to blocking anode 326-1. An example of the blocking current is approximately 5 mA. At 804, an initial amount of flanking current to each of flanking anodes 326-2, 326-3, and 326-4. The "blocking current" refers to the current flowing from the cathode to the blocking anode. The "flanking current" refers to the current flowing from the cathode to a flanking anode. In one embodiment, separate current sources are used to provide the blocking and flanking currents. In another embodiment, a single current source is used to provide the blocking and flanking currents, with the distribution of the currents among the anodes controlled by the mechanical parameters of the anodes and/or additional circuitry. The current flowing through cathode 324 is the negative sum of all the blocking and flanking currents. If the activation function is not reduced at 806, indicating insufficient neural conduction block, the blocking and/or flanking currents are increased, and/or the mechanical parameters of the anodes 326 are adjusted at 812. If the activation function is reduced at 806, indicating sufficient neural conduction block, the blocking and/or flanking currents are lowered (to allow for longer battery life of the potentially implanted neural stimulator) at 808. If the activation function is not reduced at 810, indicating insufficient neural conduction block, the blocking and/or flanking anode currents are increased, and/or the mechanical parameters of the anodes 326 are adjusted at 812. If the activation function is reduced at 810, indicating sufficient neural conduction block, the blocking and/or flanking currents are further lowered at 808. Steps 806, 808, 810, and 812 are reiterated until the electrical and mechanical parameters providing for a satisfactory performance of the neural conduction block at an approximately minimum amount of current is obtained.

Figure 9:
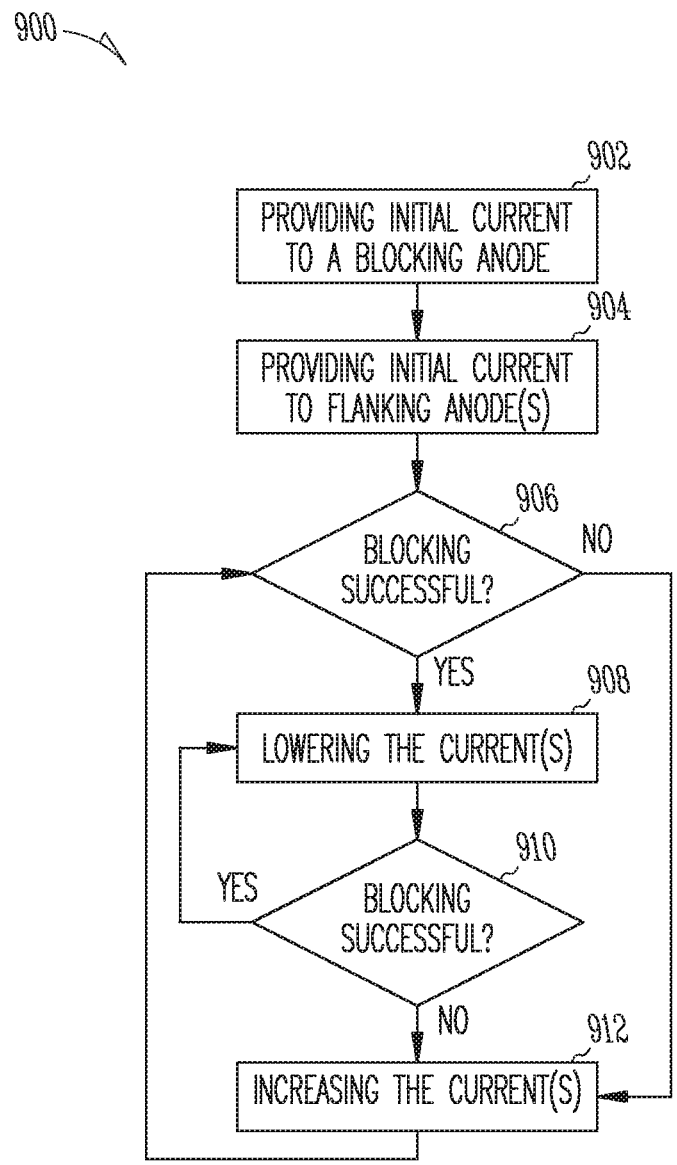
FIG. 9 is a flow chart illustrating a method for determining stimulation intensity for using the nerve cuff electrode of FIG. 7.

FIG. 9 is a flow chart illustrating a method 900 for determining stimulation intensity for using nerve cuff electrode 320 as illustrated in FIG. 7, with mechanical parameters being predetermined (such as by using method 800). At 902, an initial amount of blocking current is applied to blocking anode 326-1. An example of the blocking current is approximately 5 mA. At 904, an initial amount of flanking current to each of flanking anodes 326-2, 326-3, and 326-4. The current flowing through cathode 324 is the negative sum of all the blocking and flanking currents. If the neural conduction block is indicated to be successful at 906, the blocking and/or flanking anode currents are increased at 912. If the neural conduction block is indicated to be unsuccessful at 906, the blocking and/or flanking currents are lowered (to allow for longer battery life of the potentially implanted neural stimulator) at 908. If the neural conduction block is indicated to be unsuccessful at 910, the blocking and/or flanking anode currents are increased at 912. If the neural conduction block is indicated to be successful at 910, the blocking and/or flanking currents are further lowered at 908. Steps 906, 908, 910, and 912 are reiterated until the minimum intensity of the neural stimulation fir a satisfactory performance of the neural conduction block is obtained.

In some embodiments, the blocking and/or flanking currents are provided with separate current sources (output channels). In other embodiments, the blocking and/or flanking currents are provided with a single current source (output channel), and their distribution is controlled by the mechanical parameters of the nerve cuff electrode, as further discussed below with references to FIGS. 10-15.

Electrode Examples for Directed Promotion with Single Current Source

In various embodiments, the directed propagation of the evoked action potentials is achieved using a single output channel (current source), with system 200 configured as illustrated in FIG. 2. Examples of the nerve cuff electrode allowing for this approach are discussed with references to FIGS. 10-15. In various embodiments, a nerve cuff electrode allowing for this approach includes a cathode and a plurality of anodes. The plurality of anodes includes a blocking anode and one or more flanking anodes. The cathode and the plurality of anodes are electrically connected to a single output channel through a cathode conductor connected between the cathode and the output channel and an anode conductor connected between the plurality of anodes and the output channel, respectively, such as illustrated in FIG. 2. This allows for directed propagation with one output channel and as few as two conductors connecting between the implantable neural stimulator and the nerve cuff electrode, thereby minimizing system components, simplifying production process, and increasing system reliability. In one embodiment, a single lead includes the cathode conductor and the anode conductor. In another embodiment, a first lead includes the cathode conductor, and a second lead includes the anode conductor.

In various embodiments, the anodes are electrically connected and sized and arranged to allow the electrical stimulation pulses to provide a graded electric field in and around the portion of nerve 101 wrapped within the nerve cuff electrode to allow for the directed propagation of the evoked action potentials along nerve 101 using the mechanical parameters of the nerve cuff electrode. A desirable graded electric field is achieved in and around the portion of nerve 101 wrapped within the nerve cuff electrode by manipulating one or more mechanical parameters of the nerve cuff electrode such as parameters defining the shape, size, and location of the cathode, the number of the anodes, and the shape, size, and location of each of the anodes.

Example 1: Impedance-Coupled Anodes

FIG. 10 is an illustration of an embodiment of a nerve cuff electrode 1020 with impedance coupled anodes. Nerve cuff electrode 1020 is another example of nerve cuff electrode 220 and includes a cathode 1024 and a plurality of anodes 1026. Cathode 1024 is an example of cathode 224 and configured to be connected to cathode conductor 204C. Anodes 1026 are an example of anodes 226 and configured to be connected to anode conductor 204A. In the illustrated embodiment, anodes 1026 include a blocking electrode 1026-1 and a flanking electrode 1026-2. An impedance circuit 1040 is coupled between blocking electrode 1026-1 and flanking anode 1026-2 to provide fixed or adjustable impedance. The impedance determines the distribution of the current from cathode 1024 in anodes 1026. In one embodiment, impedance circuit 1040 includes a resistor having a preset resistance to provide a predetermined current distribution in anodes 1026. In another embodiment, impedance circuit 1040 includes a resistor having an adjustable resistance, as illustrated in FIG. 10, to provide an adjustable current distribution in anodes 1026. In the illustrated embodiment, impedance circuit 1040 is incorporated into nerve cuff electrode 1020. In another embodiment, impedance circuit 1040 is included in implantable neural stimulator 210, but that requires an additional anode conductor in lead 202 (i.e., more than one conductor 204A).

Example 2: Anodes Formed by Multi-Size Contacts

Figure 12:
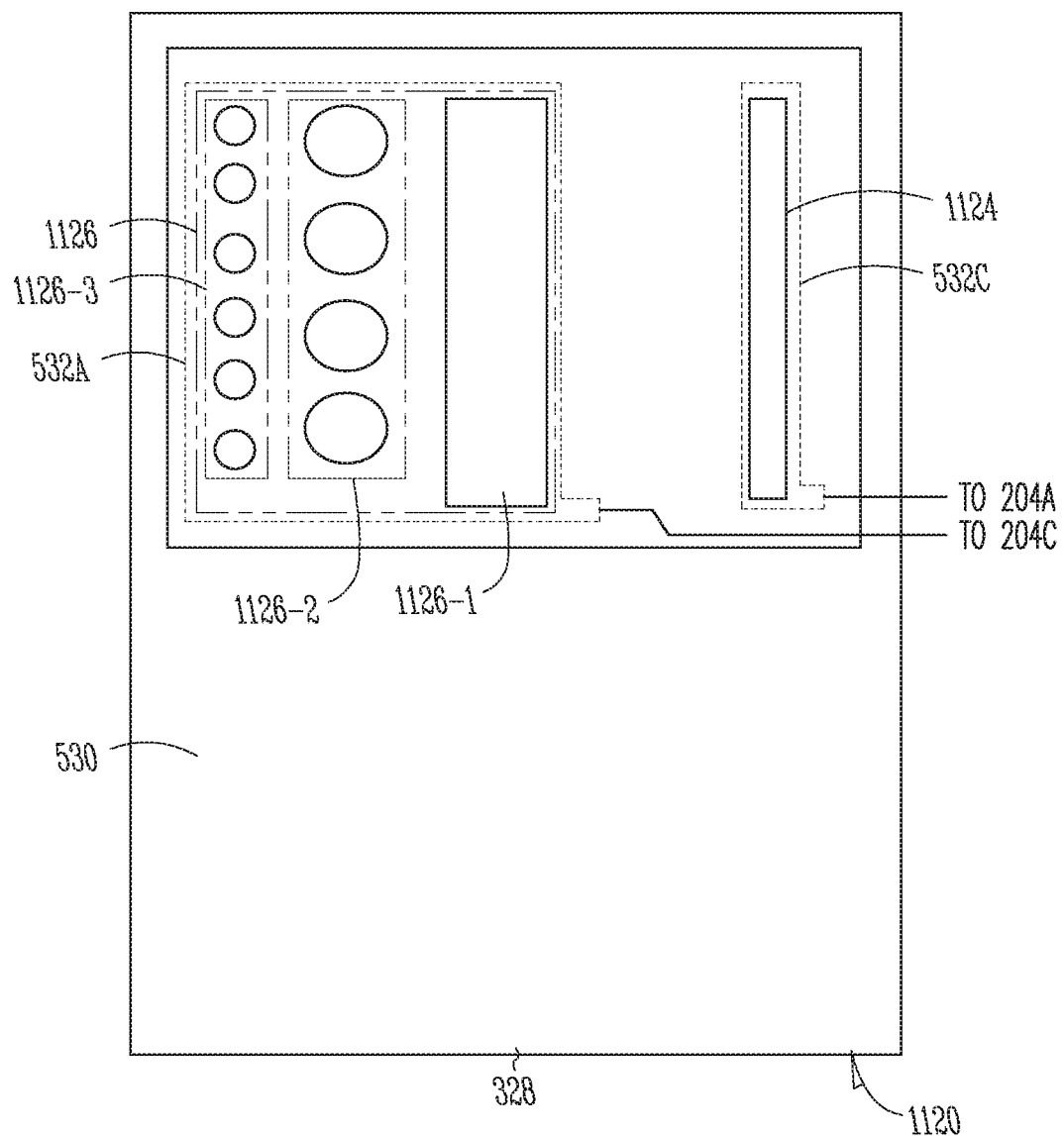
FIG. 12 is an illustration of an embodiment of the nerve cuff electrode of FIG. 11 shown in an open (uncurled) state.

FIG. 11 is an illustration of an embodiment of a nerve cuff electrode 1120 with anodes each including an array of conductive contacts. FIG. 12 is an illustration of an embodiment of nerve cuff electrode 1120 shown in an open (uncurled) state with the mechanical parameters indicated for various features. Nerve cuff electrode 1120 includes a cathode 1124 and a plurality of anodes 1126. Cathode 1124 is another example of cathode 224 and configured to be connected to cathode conductor 204C. Anodes 1126 are another example of anodes 226 and configured to be connected to anode conductor 204A. In the illustrated embodiment, anodes 1126 include a blocking anode 1126-1 and flanking anodes 1126-2 and 1126-3. Flanking anodes 1126-2 and 1126-3 each including an array of conductive contacts.

As illustrated in FIG. 12, nerve cuff electrode 1120 includes cuff substrate 328. A conductive layer 532C and a separate conductive layer 532A are affixed onto cuff substrate 328, and insulation layer 530 is affixed onto at least conductive layers 532C and 532A. Insulation layer 530 includes an opening exposing a portion of conductive layer 532C to form cathode 1124, an opening exposing a portion of conductive layer 532A to form blocking 1126-1, an array of openings exposing portions of conductive layer 532A to form flanking anode 1126-2, and another array of openings exposing portions of conductive layer 532A to form flanking anode 1126-3. Conductive layer 532C is to be electrically connected to cathode conductor 204C, such that cathode 1124 is electrically connected to cathode conductor 204C. Conductive layer 532A is to be electrically connected to anode conductor 204A, such that all of anodes 1126-1, 1126-2, and 1126-3 are electrically connected to anode conductor 204A.

In the illustrated embodiment, flanking anode 1126-2 includes a first array of conductive contacts each having a first size, and flanking anode 1126-3 includes a second array of conductive contacts each having a second size that is substantially different from the first size. In various embodiments, the size area) of each conductive contact determines the impedance of the anode and hence the distribution of the current from cathode 1124 in anodes 1126. Thus, the desirable current distribution in anodes 1126 can be achieved by manipulating the size(s) of the conductive contacts of each anode that includes an array of conductive contacts.

Example 3: Funnel Cuff

Figure 13:
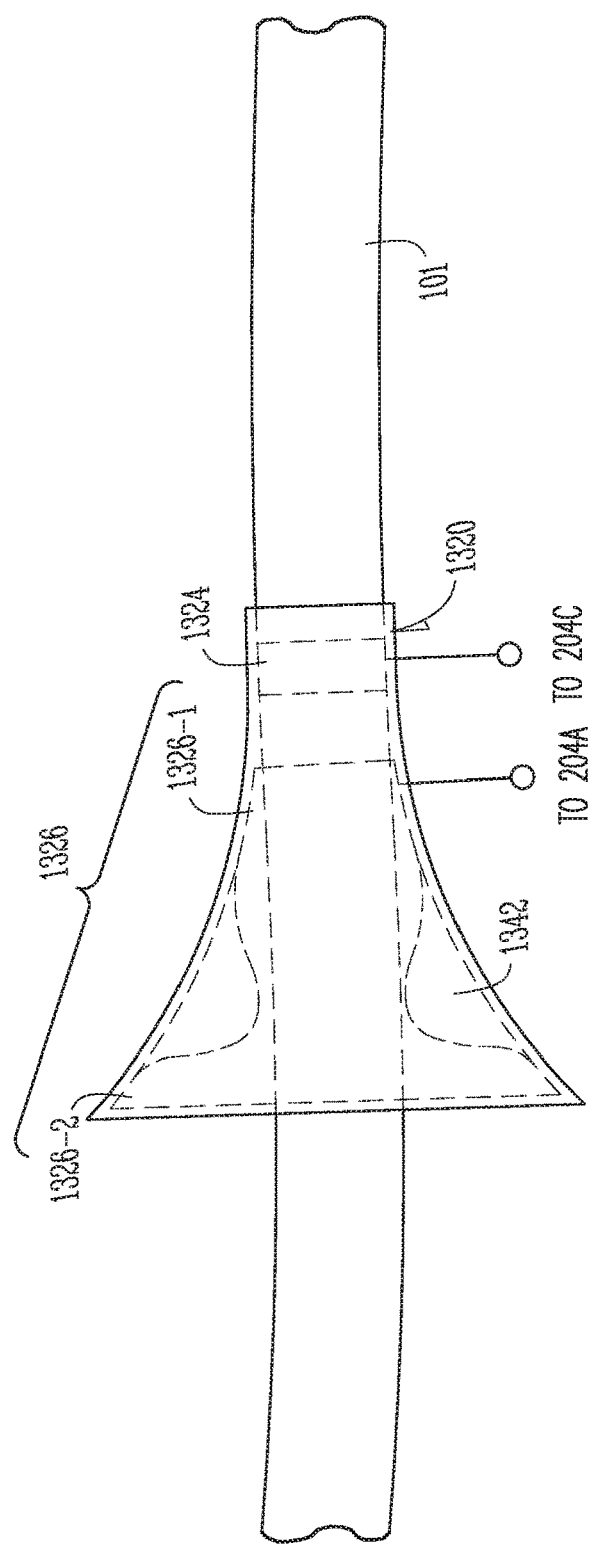
FIG. 13 is an illustration of an embodiment of a funnel-shaped nerve cuff electrode.
Figure 14:
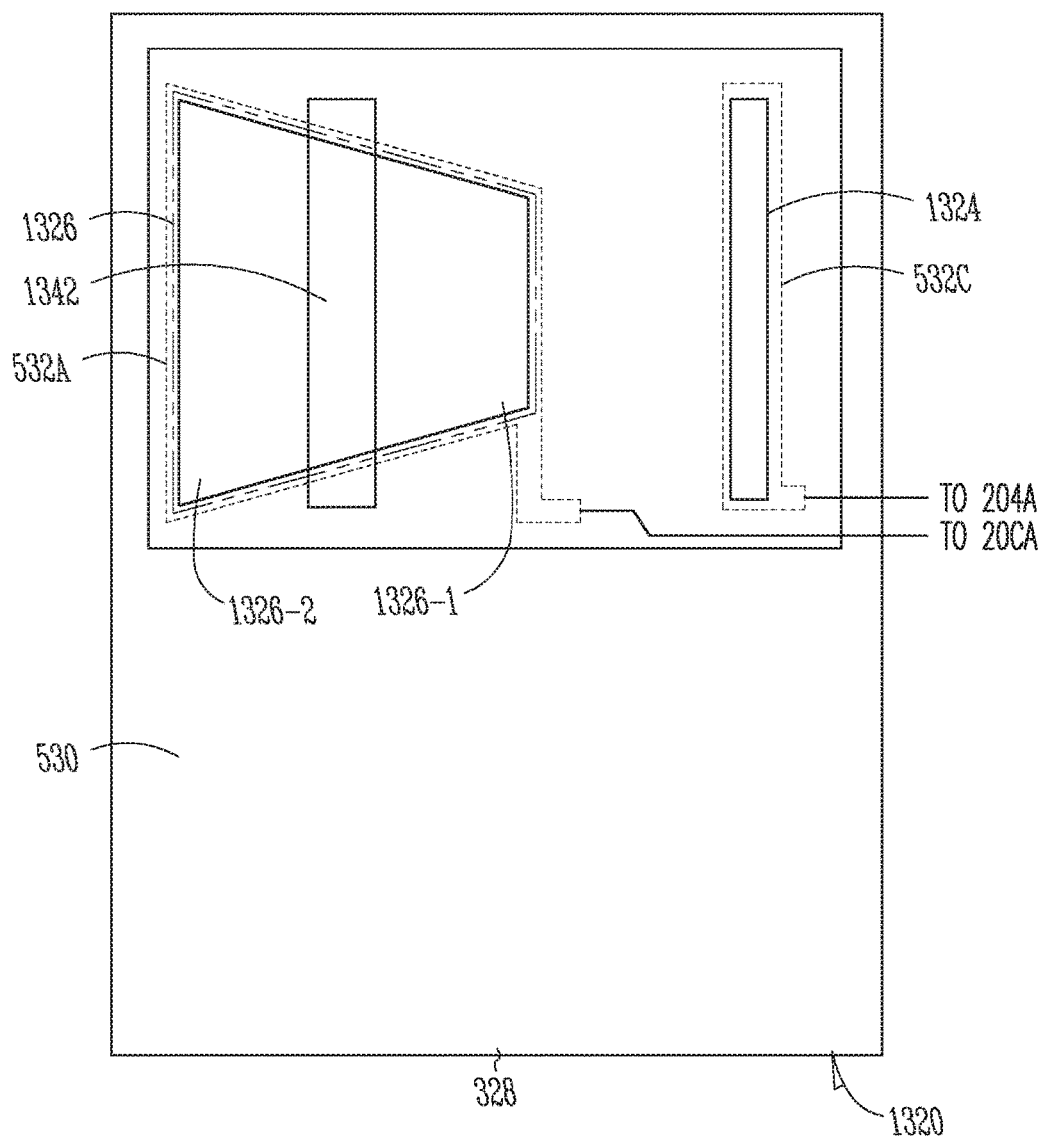
FIG. 14 is an illustration of an embodiment of the nerve cuff electrode of FIG. 13 shown in an open (uncurled) state.

FIG. 13 is an illustration of an embodiment of a funnel-shaped nerve cuff electrode 1320. FIG. 14 is an illustration of an embodiment of nerve cuff electrode 1320 shown in an open (uncurled) state with the mechanical parameters indicated for various features. Nerve cuff electrode 1320 includes a cathode 1324 and a plurality of anodes 1326. Cathode 1324 is another example of cathode 224 and configured to be connected to cathode conductor 204C. Anodes 1126 are another example of anodes 226 and configured to be connected to anode conductor 204A. In the illustrated embodiment, anodes 1326 include a blocking anode 1326-1 and a flanking anode 1326-2.

Nerve cuff electrode 1120 includes cuff substrate 328, which in the illustrated embodiment is configured to be funnel-shaped when wrapped around the portion of nerve 101 at the stimulation site. As illustrated in FIG. 14, a conductive layer 532C is affixed onto cuff substrate 328 to form cathode 1324. Another conductive layer 532A is affixed onto cuff substrate 328, and an insulation layer 1342 is affixed onto conductive layer 532A to form anodes 1326-1 and 1326-2. Insulation layer 1342 have a thickness (height) suitable for centering the portion of nerve 101 with respect to nerve cuff electrode 1320 wrapping around the portion of the nerve. In one embodiment, insulation layer 1342 is made of silicone gel. Conductive layer 532C is to be electrically connected to cathode conductor 204C, such that cathode 1324 is electrically connected to cathode conductor 204C. Conductive layer 532A is to be electrically connected to anode conductor 204A, such that both of anodes 1126-1 and 1126-2 are electrically connected to anode conductor 204A.

Figure 15:
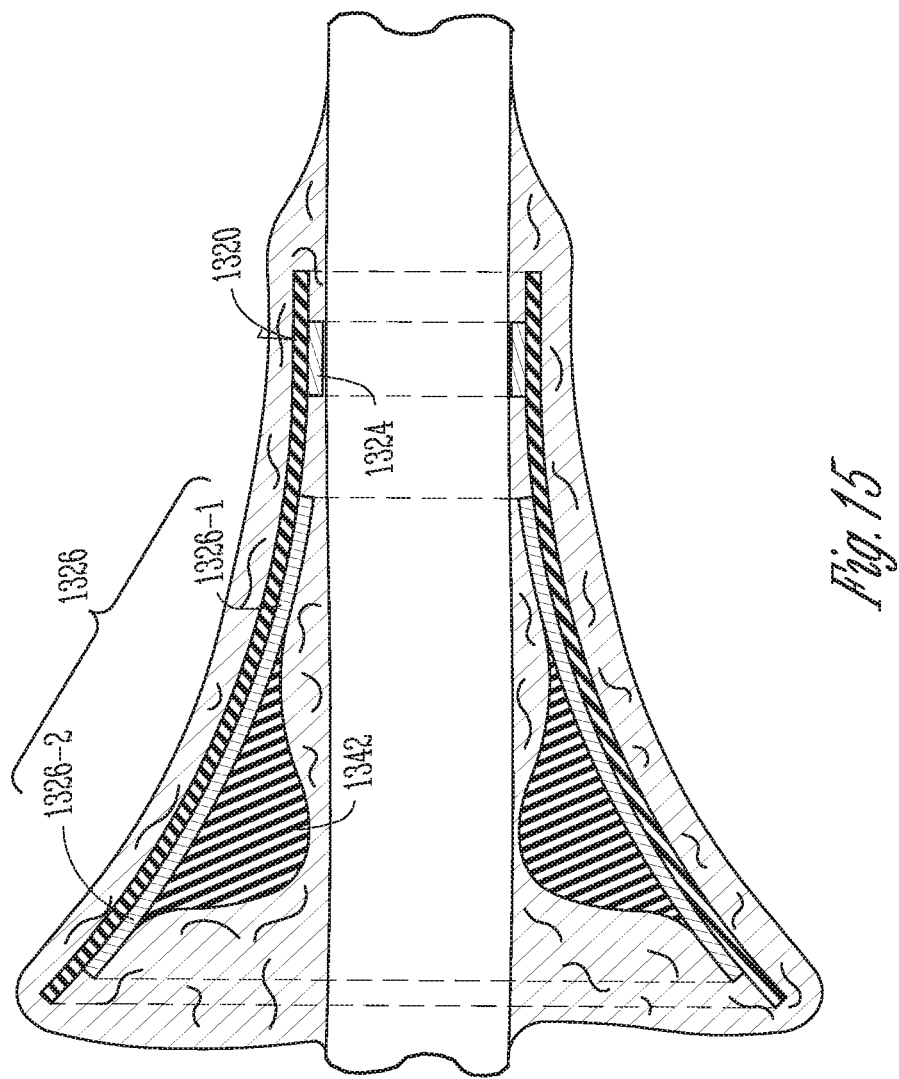
FIG. 15 is an illustration of an embodiment of the nerve cuff electrode of FIG. 13 in a cross-sectional view showing portions of the environment after implantation of the electrode.

FIG. 15 is an illustration of an embodiment of nerve cuff electrode 1320 shown in a cross-sectional view with portions of the environment after implantation of the electrode, including tissue encapsulation of nerve cuff electrode 1320 and ingrowth of tissue into spaces between nerve cuff electrode 1320 and nerve 101. The distance between each of anodes 1326 and nerve 101 allows for controlled ingrowth of connective tissue determining impedance between that anode and nerve 101, and the impedances each between one of anodes 1326 and nerve 101 determine the distribution of the current flowing from cathode 1324 in anodes 1326.

Figure 16:
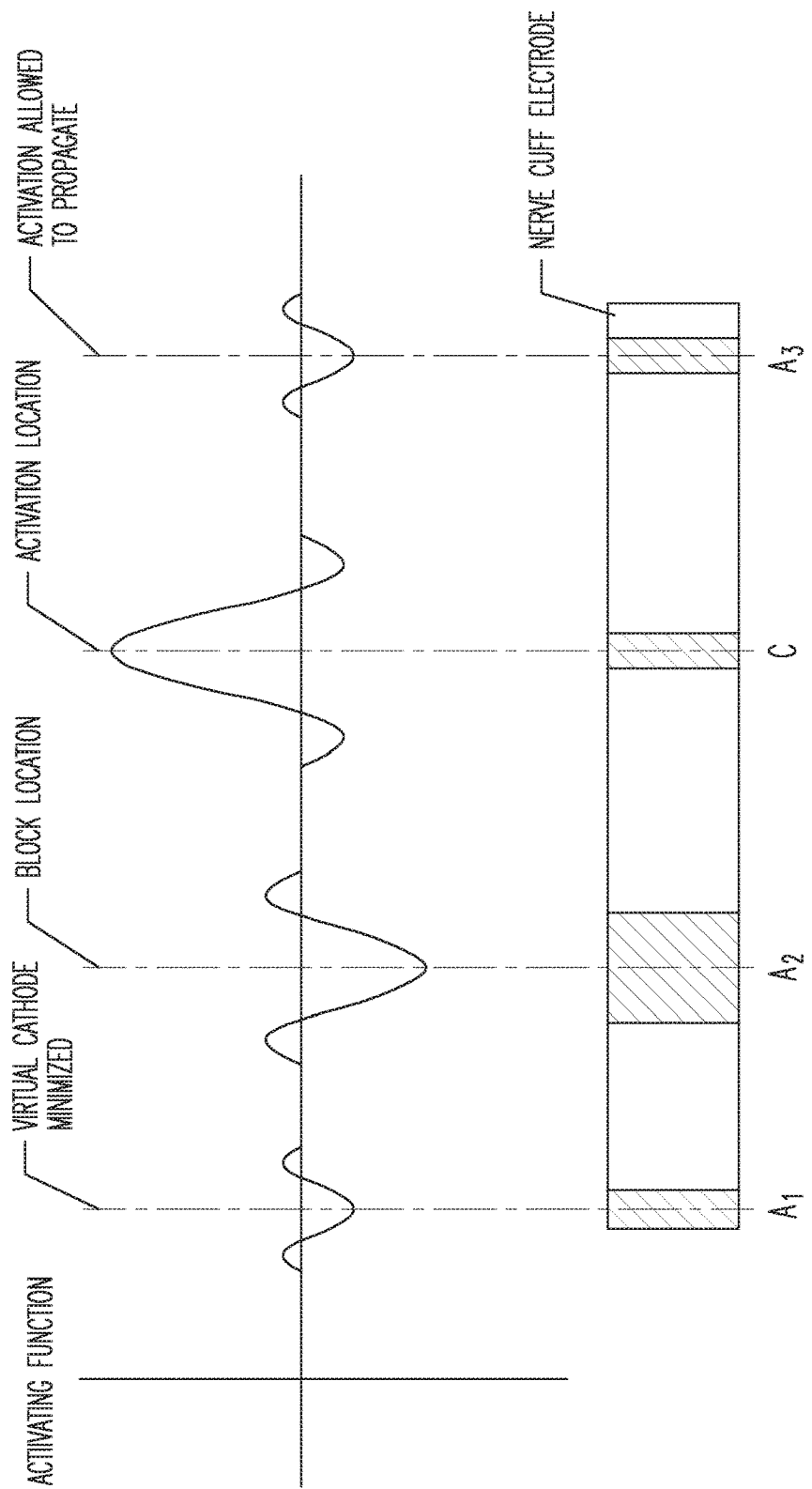
FIG. 16 is an illustration showing an example of activation function associated with an embodiment of the nerve cuff electrode.

Nerve cuff electrodes 120, 220, 320, 520, 620, 1020, 1120, and 1320 are discussed by way of example, but not by way of limitation, of the nerve cuff electrode according to various embodiments. Simulation of the neural conduction block using a quad-polar nerve cuff electrode model is performed using MATLAB®, for acute and chronic applications. The quad-polar nerve cuff electrode model including a cathode, a blocking anode, and two flanking anodes is used in the simulations. FIG. 16 is an illustration showing an example of activation function associated with such a quad-polar nerve cuff electrode including a cathode C, a blocking anode $A_2$, and two flanking anodes $A_1$ and $A_3$. When neural stimulation is applied to a nerve using the nerve cuff electrode, the electrical stimulation pulses each depolarize the membrane of the nerve at the site of cathode C (activation location) to evoke an action potential, and hyperpolarize the membrane of the nerve at the site of blocking anode $A_2$ (block location) to block propagation of the evoked action potential traveling from cathode C to blocking anode $A_2$. In the illustrated example, formation of virtual cathode is minimized at the site of flanking anode $A_1$ with the activation (evoked action potential) is allowed to propagation through the site of flanking anode $A_3$.

Results from the simulations show, among other things, that all of central and peripheral fibers of the target nerve can be blocked with none re-excited, fibers can be blocked throughout the entire diameter of the target nerve (no "bleed through" in the center of the target nerve) using a wide blocking anode, virtual cathodes can be minimized by optimizing electrode locations and currents, and edge effects can be minimized using one or more flanking anodes. Acute animal experiments with the neural stimulation delivered to the vagus nerve confirmed the simulation results by showing that the neural conduction block is achieved in A-type fibers in two out of two animals and three out of three nerves, activation of B-type fibers are maintained continuously, reliable graded and complete blocking are achieved, unbalanced quad-polar electrodes allow blocking current at 3 mA, no upper limit to stimulation and blocking currents was found, and virtual cathodes can be minimized (indicating chronic feasibility).

In various embodiments, after the implantation of the nerve cuff electrode into a patient, the tissue encapsulation and saline layer around the nerve cuff electrode may have substantial impact on activation and creation/location of virtual cathodes and anodes. Control of the healing process may increase consistency in the encapsulation and saline layer between patients. In various embodiments, a drug or combination of drug and polymer may be coated on the cathode, the anodes, the cuff substrate, inner portion of the nerve cuff electrode, outer portion of the nerve cuff electrode, edges of the nerve cuff electrode, or any combination of these areas, using a coating technology similar to the coating technology for the drug-coated stent. Controlled dissolution of the coating can account different activation at different times after the implantation of the nerve cuff electrode.

In various embodiments, the techniques of neural conduction block using the multi-polar electrode as discussed above can be combined with other techniques of unidirectional neural stimulation or block in a neural stimulation system. For example, different techniques of blocking can be applied for simultaneously controlling directions of evoked action potential propagation in different types of nerve fibers. In addition to the techniques using the multi-polar electrode as discussed above, examples of unidirectional neural stimulation or block include, but are not limited to, techniques of depletion block, such as discussed in U.S. Patent Application No. 61/928,707, entitled "SYSTEMS AND METHODS FOR SELECTIVE STIMULATION OF NERVE FIBERS IN CAROTID SINUS", filed on Jan. 17, 2014, U.S. Patent Application No. 61/928,714, entitled "SYSTEMS AND METHODS FOR DELIVERING PULMONARY THERAPY", filed on Jan. 17, 2014, Patent Application No. 61/928,725, entitled "DEPLETION BLOCK TO BLOCK. NERVE COMMUNICATION", filed on Jan. 17, 2014, and U.S. Patent Application No. 61/928,732, entitled "SELECTIVE NERVE STIMULATION USING PRESYNAPTIC TERMINAL DEPLETION BLOCK", filed on Jan. 17, 2014, which are incorporated herein by reference in their entirely.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the fill scope of equivalents to which such claims are entitled.

What is claimed is:

1. A system for delivering stimulation to a nerve at a stimulation site, comprising:
    an electrode configured to deliver electrical stimulation pulses to the nerve at the stimulation site, the electrode including:
    a substrate;
    a cathode formed on the substrate, the cathode configured to allow the electrical stimulation pulses to evoke action potentials; and
    a plurality of anodes formed on the substrate and electrically connected to each other through a conductor on the substrate, the plurality of anodes including a blocking anode and one or more flanking anodes, the blocking anode including a blocking anode conductive contact positioned adjacent to the cathode to block an unwanted propagation of the evoked action potentials in one or more fiber types of the nerve in a direction from the cathode to the blocking anode, the one or more flanking anodes positioned to minimize formation of a virtual cathode, the one or more flanking anodes each having an array of flanking anode conductive contacts and including at least one flanking anode positioned adjacent to the blocking anode such that the blocking anode is between the at least one flanking anode and the cathode, the blocking anode conductive contact and the flanking anode conductive contacts having sizes each determined to provide the plurality of anodes with impedances controlling a distribution of a current in the plurality of anodes to result in the blocking of the unwanted propagation of the evoked action potentials and the minimization of the formation of the virtual cathode.

2. The system of claim 1, wherein the electrode comprises a nerve cuff electrode, the substrate comprises a cuff substrate including a self-curling sheet configured to be wrapped around a portion of the nerve at the stimulation site, the cathode and the plurality of anodes comprise one or more ring electrodes each configured to encircle the nerve, and the plurality of anodes is arranged to effect the neural conduction block substantially within the portion of the nerve wrapped within the nerve cuff electrode.

3. The system of claim 2, wherein the one or more flanking anodes comprise a first flanking anode and a second flanking anode, the first flanking anode positioned adjacent to the blocking anode such that the blocking anode is between the first flanking anode and the cathode, the second flanking anode positioned adjacent to the first flanking anode such that the first flanking anode is between the second flanking anode and the blocking anode.

4. The system of claim 2, wherein the plurality of anodes is arranged to block propagation of the evoked action potentials from the cathode uni-directionally in the nerve while minimizing the formation of the virtual cathode.

5. The system of claim 2, wherein the plurality of anodes is arranged to allow the electrical stimulation pulses to provide a graded electric field in and around the portion of the nerve wrapped within the nerve cuff electrode.

6. The system of claim 5, further comprising an impedance circuit coupled between the blocking anode and the at least one flanking anode to further control the distribution of the current in the plurality of anodes.

7. The system of claim 6, wherein the impedance circuit comprises a resistor incorporated into the nerve cuff electrode.

8. The system of claim 5, wherein the nerve cuff electrode comprises:
    a conductive sheet on a portion of the cuff substrate; and
    an insulation sheet over the conductive sheet, the insulation sheet including openings exposing portions of the conductive sheets to form the plurality of anodes, the openings including one or more array of openings to form the one or more flanking anodes each including the array of flanking anode conductive contacts.

9. The system of claim 8, wherein the one or more flanking anodes comprise a first flanking electrode including a first array of first flanking anode conductive contacts and a second flanking electrode including a second array of second flanking anode conductive contacts, the first flanking anode conductive contacts substantially bigger than the second flanking anode conductive contacts.

10. The system of claim 5, wherein the cuff substrate is configured to be funnel-shaped when being wrapped around the portion of the nerve at the stimulation site, and the nerve cuff electrode comprises:
    a conductive sheet on the cuff substrate; and
    one or more insulation layers on a portion of the conductive sheet, the one or more insulation layers configured to center the portion of the nerve with respect to the nerve cuff electrode and expose portions of the conductive sheet to form the plurality of anodes, such that each anode of the plurality of anodes is separated from the nerve by a distance allowing for controlled ingrowth of connective tissue between the each anode and the nerve when the nerve cuff electrode is wrapped around the portion of the nerve at the stimulation site.

11. The system of claim 5, further comprising:
    an implantable neural stimulator including a pulse output circuit configured to deliver the electrical stimulation pulses, the pulse output circuit including one or more independently controllable output channels; and
    one or more leads configured to connect the nerve cuff electrode to the implantable neural stimulator, the one or more leads including a cathode conductor and an anode conductor, the cathode conductor configured to provide an electrical connection between the cathode and an output channel of the one or more output channels, the anode conductor configured to provide electrical connections between the plurality of anodes and the output channel of the one or more output channels.

12. A method for delivering stimulation to a nerve at a stimulation site, comprising:
    providing a substrate;
    positioning a cathode and a plurality of anodes on the substrate to form a stimulation electrode for delivering electrical stimulation pulses to the nerve at the stimulation site, the cathode positioned to allow the electrical stimulation pulses to evoke action potentials, the plurality of anodes electrically connected to each other and including a blocking anode and one or more flanking anodes, the blocking anode positioned adjacent to the cathode to block propagation of the evoked action potentials in one or more fiber types of the nerve in a direction from the cathode to the blocking anode, the one or more flanking anodes positioned to control formation of virtual cathode, the one or more flanking anodes including at least one flanking anode positioned adjacent to the blocking anode such that the blocking anode is between the at least one flanking anode and the cathode; and determining mechanical parameters of the stimulation electrode, including determining sizes of conductive contacts of the plurality of anodes to provide the plurality of anodes with impedances controlling a distribution of a current in the plurality of anodes such that action potentials are evoked in a portion of the nerve adjacent the cathode and neural conduction block is effected while formation of a virtual cathode is minimized, the conductive contacts including a blocking anode conductive contact of the blocking anode and each conductive contact of an array of flanking anode conductive contacts for each of the one or more flanking anodes, the neural conduction block including blocking of propagation of the evoked action potentials in one or more fiber types in the direction from the cathode to the blocking anode.

13. The method of claim 12, wherein the stimulation electrode comprises an nerve cuff electrode, the substrate comprises a cuff substrate including a self-curling sheet configured to be wrapped around a portion of the nerve at the stimulation site, and determining mechanical parameters of the stimulation electrode comprises determining the sizes and arrangement of the cathode and the plurality of anodes such that action potentials are evoked in the portion of the nerve adjacent the cathode and neural conduction block is effected substantially within the portion of the nerve wrapped within the nerve cuff electrode without forming the virtual cathode.

14. The method of claim 13, wherein determining mechanical parameters of the stimulation electrode comprises determining mechanical parameters of the stimulation electrode to block propagation of the evoked action potentials from the cathode uni-directionally in the nerve without forming the virtual cathode.

15. The method of claim 14, wherein determining the mechanical parameters of the stimulation electrode comprises:
providing an initial amount of blocking current to the blocking anode, the blocking current flowing from the cathode to the blocking anode;
providing an initial amount of flanking current to each flanking anode of the one or more flanking electrodes, the flanking current flowing from the cathode to the each flanking anode; and
adjusting geometrical parameters of the cathode and the plurality of anodes in response to the neural conduction block not being effected.

16. The method of claim 13, wherein forming the cathode and the plurality of anodes comprises forming the plurality of anodes in a manner allowing the electrical stimulation pulses to provide a graded electric field in and around the portion of the nerve wrapped within the nerve cuff electrode.

17. The method of claim 16, comprising further controlling distribution of current in the plurality of anodes using an impedance coupled between the blocking anode and the at least one flanking anode.

18. The method of claim 16, further comprising:
affixing a conductive sheet on a portion of the cuff substrate; and
affixing an insulation sheet over the conductive sheet, the insulation sheet including openings exposing portions of the conductive sheets to form the plurality of anodes, the openings including one or more array of openings to form the one or more flanking anodes each including the array of flanking anode conductive contacts.

19. The method of claim 16, further comprising:
affixing a conductive sheet on the cuff substrate; and
affixing one or more insulation bands on a portion of the conductive sheet, the one or more insulation bands configured to center the portion of the nerve with respect to the nerve cuff electrode and expose portions of the conductive sheet to form the plurality of anodes, such that each anode of the plurality of anodes is separated from the nerve by a distance allowing for controlled ingrowth of connective tissue between the each anode and the nerve when the nerve cuff electrode is wrapped around the portion of the nerve at the stimulation site.

20. The method of claim 12, comprising:
providing an initial amount of blocking current to the blocking anode, the blocking current flowing from the cathode to the blocking anode;
providing an initial amount of flanking current to each flanking anode of the one or more flanking electrodes, the flanking current flowing from the cathode to the each flanking anode;
increasing one or more of the blocking current and the flanking current in response to the neural conduction block not being effected; and
decreasing one or more of the blocking current and the flanking current in response to the neural conduction block being effected.

* * * * *